United States Patent
Sung et al.

(10) Patent No.: US 10,954,206 B2
(45) Date of Patent: Mar. 23, 2021

(54) GLYCIDYL ESTER COMPOUND PREPARATION METHOD

(71) Applicant: KOLON INDUSTRIES, INC., Seoul (KR)

(72) Inventors: Jong Un Sung, Yongin-si (KR); Sang Youb Seong, Yongin-si (KR); Yu Sung Kim, Yongin-si (KR); Jun Hyo Park, Yongin-si (KR)

(73) Assignee: KOLON INDUSTRIES, INC., Seoul (KR)

( * ) Notice: Subject to any disclaimer, the term of this patent is extended or adjusted under 35 U.S.C. 154(b) by 232 days.

(21) Appl. No.: 16/089,202

(22) PCT Filed: Mar. 27, 2017

(86) PCT No.: PCT/KR2017/003266
§ 371 (c)(1),
(2) Date: Sep. 27, 2018

(87) PCT Pub. No.: WO2017/171329
PCT Pub. Date: Oct. 5, 2017

(65) Prior Publication Data
US 2020/0299247 A1    Sep. 24, 2020

(30) Foreign Application Priority Data
Mar. 31, 2016   (KR) .................. 10-2016-0039643

(51) Int. Cl.
*C07D 301/30*   (2006.01)

(52) U.S. Cl.
CPC .................. *C07D 301/30* (2013.01)

(58) Field of Classification Search
CPC ........................ C07D 301/30; C07D 301/27
USPC ......................................... 549/515
See application file for complete search history.

(56) References Cited

U.S. PATENT DOCUMENTS

| | | | |
|---|---|---|---|
| 3,075,999 A | 1/1963 | June et al. | |
| 6,433,217 B1 | 8/2002 | Rosenbrand et al. | |
| 8,802,872 B2 * | 8/2014 | Gouman | C07D 303/16 549/515 |
| 2012/0095244 A1 | 4/2012 | Gouman et al. | |
| 2014/0316030 A1 | 10/2014 | Le Fevere de Ten Hove et al. | |

FOREIGN PATENT DOCUMENTS

| | | |
|---|---|---|
| EP | 0 610 987 A1 | 8/1994 |
| JP | 2003-171371 A | 6/2003 |
| KR | 10-2001-0090503 A | 10/2001 |
| KR | 10-0296249 B1 | 10/2001 |
| KR | 10-2012-0016313 A | 2/2012 |
| KR | 10-2015-0123991 A | 11/2015 |
| KR | 10 2016 0028494 A | 3/2016 |
| WO | 97/44335 A1 | 11/1997 |
| WO | 00/17179 A1 | 3/2000 |

OTHER PUBLICATIONS

International Search Report for PCT/KR2017/003266 dated Jul. 17, 2017 [PCT/ISA/210].

* cited by examiner

*Primary Examiner* — Charanjit Aulakh
(74) *Attorney, Agent, or Firm* — Sughrue Mion, PLLC

(57) ABSTRACT

The present invention relates to a method for preparing a glycidyl ester compound which comprises performing a reaction under reduced pressure without using a reaction solvent.

10 Claims, No Drawings

GLYCIDYL ESTER COMPOUND PREPARATION METHOD

TECHNICAL FIELD

This application is a National Stage of International Application No. PCT/KR2017/003266, filed on Mar. 27, 2017, which claims priority from Korean Patent Application No. 10-2016-0039643, filed on Mar. 31, 2016 with the Korean Intellectual Property Office, the disclosure of which is herein incorporated by reference in its entirety.

The present invention relates to a method for preparing glycidyl ester compounds.

BACKGROUND ART

Glycidyl esters are mainly used as diluents for epoxy resins with high boiling point, and they also are used to produce resin compositions of various compositions such as epoxy resin, ester resin, alkyd resin and acrylic resin by reacting with acrylic acid, polyol, polyacid, etc.

Among them, the olefin-derived glycidyl ester having a C5 to C10 alkyl group such as neodecanoic acid glycidyl ester itself is usefully used as a reactive diluent for the preparation of thermosetting acrylic acid, epoxy polyester, urethane paint and coatings.

The glycidyl ester and the method thereof are prepared by the reaction of alkali salt of carboxylic acid and epichlorohydrin, and at this time, the reaction is carried out at from 50 to 150° C. in the presence of a catalyst, an alkali salt and water. This method produces a large amount of unreacted materials with the final products and also generates a large amount of intermediates or by-products during the reaction, so that the separation of the final products was not easy.

In this connection, WO1997/044335 has proposed that the yield of glycidyl ester can be increased by removing water and by-product through vacuum distillation method. However, the vacuum distillation method has a problem that since the amount of glycidyl ester removed to obtain high purity glycidyl ester is too large, it is not preferable from the viewpoint of productivity.

As an alternative to this, Korean Patent Laid-open Publication No. 2001-0090503 discloses that the glycidyl ester can be prepared with a yield of about 90% by dissolving monocarboxylic acid and epichlorohydrin in a mixed solvent containing water and then adding a catalyst such as metal hydroxide and then reacting them.

Although the method disclosed in the above patent publication has an advantage that the glycidyl ester can be produced at a high yield, since the reactant and the solvent are used at a weight ratio of 1:1, and the amount of reactant introduced into the reactor is limited due to the solvent used, there is a limit to increase the unit output of the final glycidyl ester-based compound.

PRIOR ART LITERATURE

Patent Literature

WO1997/044335 (1997 Nov. 27), PURIFICATION OF GLYCIDYL ESTERS BY THIN FILM EVAPORATION

Korean Patent Application Publication No. 2001-0090503 (2001 Oct. 18), PROCESS FOR THE PREPARATION OF GLYCIDYLESTERS OF BRANCHED CARBOXYLIC ACIDS.

DISCLOSURE

Technical Problem

The inventors of the present invention have studied various methods for improving the unit output of the glycidyl ester compound. And they have come up with the idea that when only the reactants are used without the use of the reaction solvent in the preparation of the glycidyl ester compound, the unit output of the finally produced compound may be increased. Thereafter, they have invented a method capable of preparing the compound without using the reaction solvent through continuous research and development, thereby completing the present invention.

Accordingly, it is an object of the present invention to provide a method for producing a glycidyl ester compound, which can increase unit output and yield as compared with the conventional method.

Technical Solution

In order to solve the above object, the present invention provides a method for preparing a glycidyl ester compound represented by Formula 1, which comprises reacting a carboxylic acid compound of Formula 2 and epihalohydrin of Formula 3 under reduced pressure without using a reaction solvent, represented by the following Reaction scheme 1:

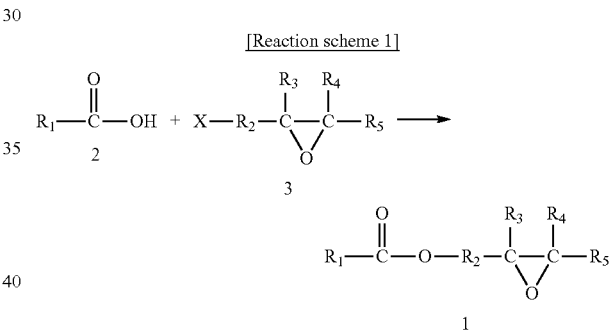

wherein $R_1$ to $R_5$, and X are as described in the specification.

Advantageous Effects

The glycidyl ester compound preparation method according to the present invention can increase the unit output of the glycidyl ester compound in the same reactor by performing the reaction under reduced pressure without using the reaction solvent to prepare the glycidyl ester compound.

In addition, the method according to the present invention produces very little side-reaction products and unreacted materials and makes it possible to produce the compound at a higher yield than conventional processes.

BEST MODE

The present invention provides a method for preparing a glycidyl ester compound without the use of reaction solvent to increase the unit output.

The "unit output" associated with the productivity of the compound is not simply a concept of yield but is the concept of the ratio of the output of the final product to the total input raw materials (including catalyst and reaction solvent).

Conventional methods for increasing the productivity of the compound have focused on improving the yield and purity. However, the present invention provides a method for increasing the unit output in the same size reactor with the above yield and purity. Specifically, the present invention provides a method in which a reaction solvent is not used. In other words, the present invention can increase the unit output of the finally produced compound by excluding the reaction solvent and supplying the reactants by an amount corresponding to that.

The preparation method of the glycidyl ester compound proposed in the prior art essentially uses the mixed solvent of water or water/isopropyl alcohol, which means that the progress of reaction cannot be expected without the solvent. However, unlike the prior art, the method according to the present invention allows the reaction to proceed without the reaction solvent to produce the glycidyl ester compound, which can be achieved by performing the reaction under reduced pressure.

The glycidyl ester compound of the present invention may be represented by Formula 1 below:

[Formula 1]

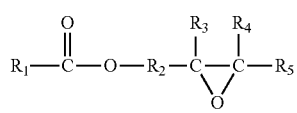

wherein $R_1$ is a C1 to C20 alkyl group, a C2 to C20 alkenyl group, a C2 to C20 alkynyl group, a C1 to C20 alkoxy group, a C3 to C20 cycloalkyl group, a C5 to C40 heteroaryl group, a C6 to C40 aryl group, a C6 to C20 alkoxyaryl group, or a C6 to C20 arylalkyl group, $R_2$ is a C1 to C20 alkylene group, C1 to C20 alkenylene group, C3 to C20 cycloalkylene group, or C6 to C40 arylene group, $R_3$ to $R_5$ are the same or different from each other and are hydrogen or a C1 to C20 alkyl group.

Preferably, $R_1$ may include a primary alkyl group, a secondary alkyl group and a tertiary alkyl group, and more preferably, may be represented by

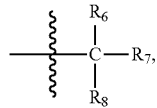

wherein $R_6$ to $R_8$ may be the same or different from each other and may be hydrogen or a C1 to C20 alkyl group and preferably may satisfy 3≤sum of carbon numbers $(R_6+R_7+R_8)$≤12 and more preferably 6≤sum of carbon numbers $(R_6+R_7+R_8)$≤12.

The term "alkyl" as used herein refers to a linear or branched saturated monovalent hydrocarbon moiety having 1 to 20, preferably 1 to 10, more preferably 1 to 6 carbon atoms. The alkyl group may be unsubstituted or further substituted by a substituent as described below. Examples of the alkyl group may include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, and the like.

The term "alkenyl" refers to a linear or branched monovalent hydrocarbon moiety containing one or more C=C double bonds and having 2 to 20, preferably 2 to 10, more preferably 2 to 6 carbon atoms. The alkenyl group can be bonded through hydrocarbons containing a C=C double bond or through saturated hydrocarbons. The alkenyl group may be unsubstituted or further substituted by a certain substituent group as described below. Examples of the alkenyl group may include ethenyl, 1-propenyl, 2-propenyl, 2-butenyl, 3-butenyl, pentenyl, 5-hexenyl, dodecenyl and the like.

The term "alkynyl" refers to a linear or branched monovalent hydrocarbon moiety containing one or more C≡C triple bonds and having 2 to 20, preferably 2 to 10, more preferably 2 to 6 carbon atoms. The alkynyl group can be bonded through hydrocarbons containing a C≡C triple bond or through saturated hydrocarbons. The alkynyl group can be further substituted by a constant substituent group as described below. For example, the alkynyl group may be ethynyl, propynyl, and the like.

The term "alkoxy" refers to a linear or branched saturated monovalent hydrocarbon moiety having 1 to 20, preferably 1 to 10, more preferably 1 to 6 carbon atoms. The alkoxy group may be unsubstituted or further substituted by a certain substituent group as described below. Examples of the alkoxy group may include methoxy, ethoxy, propoxy, isopropoxy, butoxy, pentoxy, heptoxy, dodecoxy, fluoromethoxy, difluoromethoxy, trifluoromethoxy, chloromethoxy, dichloromethoxy, trichloromethoxy, iodomethoxy, bromomethoxy and the like.

The term "cycloalkyl" refers to a saturated or unsaturated, monovalent non-aromatic monocyclic, bicyclic or tricyclic hydrocarbon moiety of 3 to 12 ring carbon atoms, which may be further substituted by a constant substituent as described below. For example, the cycloalkyl may be cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (i.e. bycyclo [2, 2, 1] hept-5-enyl) and the like.

The term "heteroaryl" refers to an aryl having 5 to 40, preferably 5 to 12 ring atoms, wherein at least one carbon in the ring is substituted with nitrogen (N), oxygen (O), sulfur (S), or phosphorus (P). For example, the heteroaryl refers to a monocyclic, bicyclic or more aromatic group containing 1 to 4 hetero atoms. Examples of monocyclic heteroaryls may include, but are not limited to, triazolyl, oxazolyl thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl and similar groups. Examples of bicyclic heteroaryl may include, but are not limited to, indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, furo pyridinyl and similar groups.

The term "aryl" refers to a monovalent monocyclic, bicyclic, or tricyclic aromatic hydrocarbon moiety having 6 to 40, preferably 6 to 12 ring atoms, which may be further substituted by a certain substituent as described below. Examples of the aryl group may include phenyl, naphthalenyl and fluorenyl.

The term "alkoxyaryl" refers to an aryl in which at least one hydrogen atom of the above-defined aryl group is substituted with an alkoxy group. Examples of the alkoxyaryl group may include methoxyphenyl, ethoxyphenyl, propoxyphenyl, butoxyphenyl, pentoxyphenyl, hextoxyphenyl, heptoxy, octoxy, nanoxy, methoxybiphenyl, methoxynaphthalenyl, methoxyfluorenyl or methoxyanthracenyl.

The term "arylalkyl" refers to an alkyl in which at least one hydrogen atom of the alkyl group defined above is substituted with an aryl group, which may be further substituted by a constant substituent as described below. Examples thereof may include benzyl, benzhydryl, trityl and the like.

The term "alkylene" refers to a linear or branched, saturated divalent hydrocarbon moiety having 1 to 20, preferably 1 to 10, more preferably 1 to 6 carbon atoms. The alkylene group may be further substituted by a constant substituent as described below. Examples of the alkylene group may include methylene, ethylene, propylene, butylene, hexylene and the like.

The term "alkenylene" refers to a linear or branched divalent hydrocarbon moiety containing at least one C=C double bond and having 2 to 20, preferably 2 to 10, and more preferably 2 to 6 carbon atoms. The alkenylene group can be bonded through hydrocarbons containing C=C double bonds and/or through saturated hydrocarbons. The alkenylene group can be further substituted by a constant substituent as described below.

The term "cycloalkylene" refers to a saturated or unsaturated, non-aromatic divalent monocyclic, bicyclic or tricyclic hydrocarbon moiety having 3 to 12 ring carbon atoms, which may be further substituted by a constant substituent as described below. Examples thereof may include cyclopropylene, cyclobutylene, and the like.

The term "arylene" refers to a divalent monocyclic, bicyclic or tricyclic aromatic hydrocarbon moiety having 6 to 20, preferably 6 to 12 ring atoms, which may be further substituted by a certain substituent as described below. The aromatic part contains only hydrocarbon. Examples of the arylene group may include phenylene and the like.

The term "arylalkylene" refers to a divalent moiety in which at least one hydrogen atom of the alkyl group defined above is substituted with an aryl group, which may be further substituted by a substituent group as described below. Examples thereof may include benzylene and the like.

The term "alkynylene" refers to a linear or branched divalent hydrocarbon moiety containing one or more CC triple bonds and having 2 to 20, preferably 2 to 10, more preferably 2 to 6 carbon atoms. The alkynylene group may be bonded through hydrocarbons containing a C=C triple bond or through saturated hydrocarbons. The alkynylene group may be further substituted by a constant substituent group described below. Examples thereof may include ethynylene, propynylene and the like.

In the present specification, all the compounds or substituents may be substituted or unsubstituted unless otherwise specified. The term "substituted" as used herein means that hydrogen is replaced with at least one selected from the group consisting of halogen atom, hydroxyl group, carboxyl group, cyano group, nitro group, amino group, thio group, methylthio group, alkoxy group, nitryl group, aldehyde group, epoxy group, ether group, ester group, carbonyl group, acetal group, ketone group, alkyl group, perfluoroalkyl group, cycloalkyl group, heterocycloalkyl group, allyl group, benzyl group, aryl group, heteroaryl group, derivatives thereof and combinations thereof In particular, the glycidyl ester compound of Formula 1 of the present invention may include all isomers unless otherwise stated. As such isomers, all stereoisomers, such as isomers which may exist due to asymmetric carbons on various R and Z substituents (including enantiomers (which may exist even in the absence of asymmetric carbons) and diastereomers), are contemplated within the scope of the present invention. Each stereoisomer of the compound of the present invention may be, for example, substantially free of other isomers, or may be mixed, for example, as racemates or with all stereoisomers or selected stereoisomers.

The glycidyl ester compound of Formula 1 according to the present invention is prepared by dehydration reaction of a carboxylic acid compound and an epihalohydrin compound, and this reaction is carried out in the presence of a reaction solvent and a catalyst. In the present invention, the glycidyl ester compound may be prepared under the condition that the reaction solvent is not used to increase the unit output of the glycidyl ester compound.

Specifically, the glycidyl ester compound of Formula 1 may be prepared by reacting the carboxylic acid compound of Formula 2 and the epihalohydrin of Formula 3 as shown in the following Reaction Scheme 1:

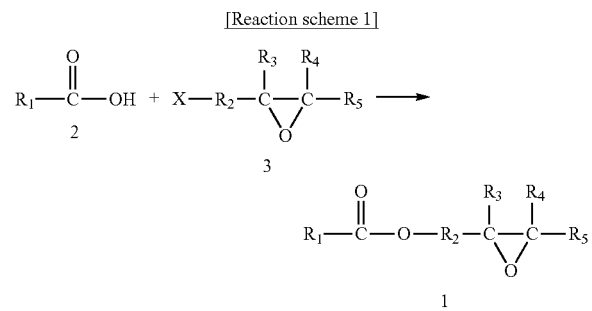

wherein $R_1$ to $R_5$ are as described in Formula 1, and X is halogen.

Preferably, X may be Cl, F, Br, or I, more preferably Cl.

More specifically, the glycidyl ester compound of Formula 1 may be prepared by performing through the following steps of, a preliminary reaction step S1) of reacting the carboxylic acid compound of Formula 2 and the epihalohydrin of Formula 3 in the presence of a base catalyst without the use of reaction solvent to perform a ring-opening reaction;

a main reaction step S2) of adding the base catalyst to the obtained reaction product and carrying out a ring-closing reaction under reduced pressure; and a step S3) of post-treating the obtained product.

Each step will be described in detail below.

S1) Preliminary Reaction Step

First, the preliminary reaction may be performed to bind the compound of Formula 2 and the compound of Formula 3, by injecting a base catalyst into a reactor and adding the carboxylic acid compound of Formula 2 and the epihalohydrin of Formula 3 and thus performing a ring-opening reaction.

The carboxylic acid compound of Formula 2 can be any compound as long as it meets the definition of $R_1$, and preferably may be neodecanoic acid, neotridecanoic acid, pivalic acid, and the like. These compounds of Formula 2 can be prepared directly or purchased commercially, and if necessary can be used after purification process in use.

The epihalohydrin compound of Formula 3 is a compound containing a halogen element (X), which can include various compounds depending on X, and may include epichlorohydrin, epibromohydrin, methylepichlorohydrin or any other known epihalohydrin, preferably epichlorohydrin.

The epichlorohydrin is a compound having a molecular formula of $C_3H_5C_{10}$, a molecular weight of 92.53 mol/g, and CAS No. 106-89-8. The epichlorohydrin is an organochlorine substance having epoxide in its structure, which is a compound with very strong reactivity, and is available from commercial sources.

In this preliminary reaction, the carboxylic acid compound and the epihalohydrin may be used in a molar ratio of from 1:1.2 to 1:5.0. When the epihalohydrin is used below the above range, the total of the compounds of Formula cannot be converted and thus the yield of the glycidyl ester compound finally obtained is lowered. On the contrary, when the ratio exceeds the above range, unreacted epihalohydrin is increased to cause a side-reaction therebetween, resulting in an increase in cost and production cost due to the use of excessive epihalohydrin.

At this time, the base catalyst is used to initiate the ring-opening reaction, and may be an alkali metal hydroxide such as LiOH, NaOH or KOH, an alkali earth metal hydroxide such as $Ca(OH)_2$ or $Mg(OH)_2$, or an alkali carbonate such as $K_2CO_3$, $Na_2CO_3$, $KHCO_3$ and $NaHCO_3$. and preferably $K_2CO_3$.

The base catalyst may be used in the range of from 0.001 to 0.01 mole relative to 1 mole of epihalohydrin of Formula 2 for sufficient catalytic reaction. When the content of the base catalyst is less than the above range, there is a concern that the yield of the reaction may decrease. On the contrary, when the content exceeds the above range, there is a concern that side reaction may occur due to excessive reaction. Therefore, it is appropriately used within the above range.

At this time, the order of injection of the base catalyst can be any time, such as before, after, or during the injection of the reactant.

Preferably, the preliminary reaction may be carried out by a mechanism as shown in the following Reaction Scheme 2. At this time, for convenience in relation to description, neopentanoic acid (or pivalic acid) is used as the compound of Formula 2, and epichlorohydrin is used as the compound of Formula 3:

[Reaction Scheme 2]

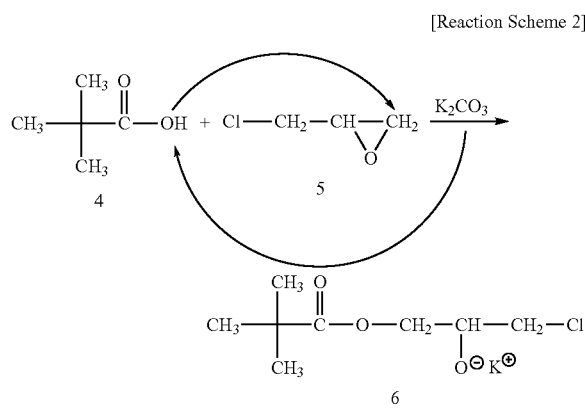

According to the Reaction Scheme 2, the neopentanoic acid of Formula 4 may be activated by the base catalyst, and the OH-ion of this compound may attack the epichlorohydrin of Formula 5 to produce a salt-form compound of Formula 6 through a ring-opening reaction.

This preliminary reaction may be carried out at from 80 to 100° C. for 0.5 to 24 hours. This temperature is for a sufficient preliminary reaction. When the temperature and time are less than the above range, the subsequent ring-closing reaction step is not sufficiently carried out and thus the yield of the compound of Formula 1 is lowered. On the contrary, when the reaction is carried out at an excessive temperature for a long time, there is a concern that a reverse reaction or a side reaction may occur.

S2) Main Reaction Step

Next, the main reaction for performing the ring-closing reaction may be performed by adding the base to the reactor and reducing the pressure. This ring-closing reaction may proceed by the mechanism of the following reaction scheme 3:

[Reaction Scheme 3]

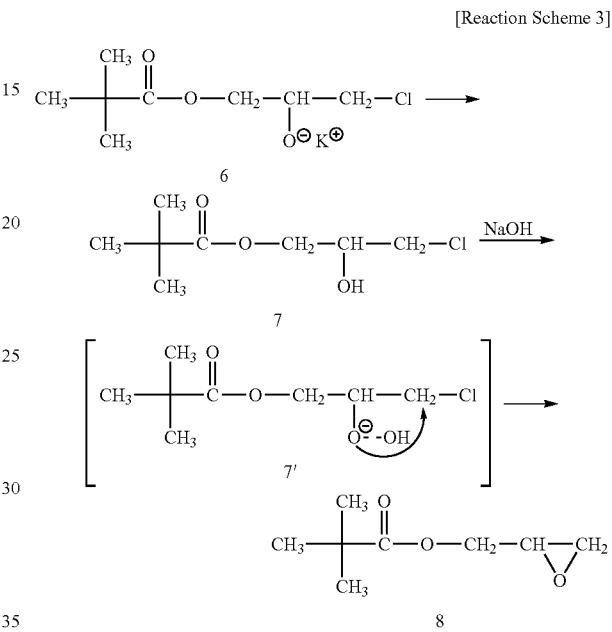

Referring to the above reaction scheme 3, the compound in the salt form of Formula 6 may be rapidly converted into the compound of Formula 7, and oxygen ion may attack the $CH_2$ of $—CH_2Cl$ by the base catalyst (transition state of Formula 7') and thus cause a ring-closing reaction between C—O to form a glycidyl ester compound of Formula 8 in which an epoxy ring is formed at the end.

At this time, the base catalyst used may be the same as or different from the base used in step S1), preferably NaOH.

The base catalyst may be used in the range of from 0.01 to 1.2 moles relative to 1 mole of the compound of Formula 7 for sufficient catalytic reaction. At this time, the content of the compound of Formula 7 presupposes that 100% of the reactants from the previous step are converted. When the content of the base catalyst is less than the above range, there is a concern that the ring-closing reaction is insufficient and thus the yield of the reaction may be lowered. On the contrary, when the content exceeds the above range, there is a concern that the side reaction may occur due to excessive reaction. Therefore, it is appropriately used within the above range.

Particularly, according to the conventional process, the main reaction in which the ring-closing reaction is performed is carried out in the presence of water or a mixed solvent of water/IPA. However, in the present invention, the reaction may be carried out without the reaction solvent, but under reduced pressure so that the ring-closing reaction can be smoothly performed.

Specifically, the main reaction may be carried out at from 35 to 90° C., preferably at from 40 to 80° C. for 0.5 to hours after reducing the pressure to 50 to 200 Torr, preferably 100 to 150 Torr. At this time, when the pressure is higher than the above range, a sufficient reaction is not performed. On the contrary, when the pressure is lower than the above range, there is a concern that a side reaction may occur.

In particular, the main reaction is a reaction in which water is produced as a product of the reaction, wherein a reverse reaction may occur due to the generated water. Therefore, in order to prevent the reverse reaction, the device used for the main reaction may use a device capable of decanting.

The glycidyl ester compound obtained by the ring-closing reaction may be subjected to a subsequent purification process, and at this time, degassing and further ring-closing reactions may be performed before the purification process.

The degassing may be carried out to remove the unreacted epihalohydrin of Formula 3 in the product obtained between the main reaction and the post-treatment. Preferably the degassing process may performed at a temperature of from 110 to 150° C. under a pressure of 10 Torr or less.

In addition, an additional ring-closing reaction may be performed by adding a base catalyst to the product obtained before the post-treatment. At this time, the type and content of the base catalyst used in the additional ring-closing reaction, the reaction condition and the like are as described above.

S3) Post-Processing Step

Next, the post-treatment to purify the product obtained in the previous step S2) may be carried out to obtain the glycidyl ester compound of Formula 1.

The post-treatment process is for removing unreacted materials and by-products of the reaction and is not particularly limited in the present invention and can be a process commonly used in the preparing process of the compound. Typically, as post-treatment, it is possible to perform any one of desalting, neutralization, water washing, filtration, purification, concentration, crystallization and drying. Preferably, the purification process may be carried out after desalting, washing and neutralization.

The purification process is not particularly limited in the present invention, and various known processes can be used. For example, the purification process may be performed by any one of simple distillation, fractional distillation, azeotropic distillation, vacuum distillation, recrystallization, extraction, sublimation or chromatography, and preferably may be performed by distillation process.

The purification using distillation method, for example, passes the resulting product through a distillation column to transfer the glycidyl ester compound to the upper connector while at the same time transporting unreacted compounds or side-reaction compounds to the lower connector of the distillation column.

In the preparation of the glycidyl ester compound through the above-mentioned method, it is possible to ensure a yield equal to or higher than that of the conventional process in terms of yield, and the unit output of the glycidyl ester compound produced per unit time in the unit batch is greatly increased by carrying out the reaction without using the reaction solvent. In addition, the method according to the present invention may produce very little side-reaction products and unreacted materials, and it is possible to prepare the compound at a higher yield than the conventional processes.

The prepared glycidyl ester compound can be applied variously as a diluent to reactivity, and also to raw materials of various compounds, intermediates, the preparation of resin and the like.

MODE FOR INVENTION

Hereinafter, preferred examples and comparative examples of the present invention will be described. However, the following examples are merely preferred examples of the present invention, and the present invention is not limited to the following examples.

EXAMPLES

Example 1: Preparation of (oxiran-2-yl)methyl pivalate

The title compound was prepared according to the following reaction scheme 4.

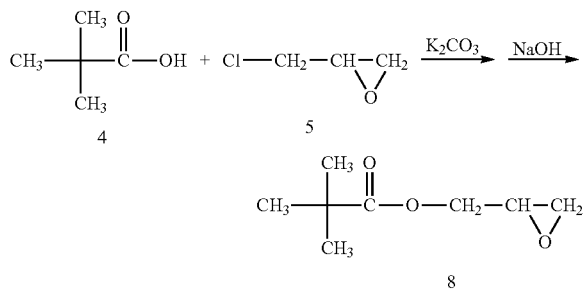

(1) Preliminary Reaction (Addition Reaction)

To a 5 L reactor, 1,000 g (5.805 mol) of neodecanoic acid (NDA) and 2, 363 g (25.543 mol) of epichlorohydrin were charged. The inside of the reactor was heated to 90° C. while being purged with nitrogen, 12.5 g (0.0904 mol) of potassium carbonate ($K_2CO_3$) were added in one portion and then the mixture was stirred for 3 hours to carry out a preliminary reaction.

(2) Main Reaction (Ring-Closing Reaction)

After the completion of the preliminary reaction, the reactor was cooled to a temperature of 60° C., and then 50 wt. % NaOH 511 g (12.772 mol) was uniformly added dropwise for hours using a funnel while maintaining the degree of vacuum of 120 to 140 Torr and 60° C. During the reaction for hours, water was generated and water was continuously removed using a decanter facility. After completing the dropwise addition of 50 wt. % NaOH, water was continuously removed with further stirring for 1 hour.

In order to remove unreacted epichlorohydrin, the reaction was performed while raising the reaction temperature to 130° C., and then degassing was carried out under 10 Torr or less. Thereafter, the amount of chlorine in the product (Hy-Cl) was measured.

After the temperature of the reactor was raised to 60° C., 17.1 g of water and 50 wt. % NaOH 11.4 g were added and stirred for 2 hours to perform an additional ring-closing reaction (for reference, 1.5 mol of NaOH/mol of hydrolysable chlorine).

At this time, if the chlorine content is 0.1% or more, further ring-closing reaction using NaOH was carried out again, and the reaction was terminated at the time of less than 0.1%.

(3) Post-Treatment

After completion of the reaction, 582 g of water was added to the obtained product and stirred for 60 minutes to induce phase separation. After standing for 1 hour, the lower aqueous phase portion was removed. The washing process was performed three times so that the pH of the aqueous phase portion to be removed was 5 to 7.

Subsequently, the oil phase of the upper layer was then recovered and degassed under a vacuum of 10 Torr at 120° C. to produce the title compound.

Example 2: Preparation of (oxiran-2-yl)methyl 2-ethylhexanoate

The title compound was prepared according to the following reaction scheme 5.

[Reaction Scheme 5]

$$H_3C-CH_2$$
$$H_3C-CH_2$$
$$H_3C-CH-C(=O)-OH +$$
$$H_3C-CH_2$$
9

$$Cl-CH_2-CH-CH_2 \xrightarrow{K_2CO_3} \xrightarrow{NaOH}$$
 \\/
 O
5

$$H_3C-CH_2$$
$$H_3C-CH_2$$
$$H_3C-CH-C(=O)-O-CH_2-CH-CH_2$$
$$H_3C-CH_2 \qquad\qquad\qquad \\/$$
$$\qquad\qquad\qquad\qquad\qquad O$$
10

(1) Preliminary Reaction

To a 5 L reactor, 1,100 g (7.627 mol) of 2-ethylhexanoic acid (2-EHA) and 3104 g (33.549 mol) of epichlorohydrin were charged. The inside of the reactor was heated to 90° C. while being purged with nitrogen, 13.8 g (0.1059 mol) of potassium carbonate ($K_2CO_3$) were added in one portion and then the mixture was stirred for 3 hours.

(2) Main Reaction (Ring-Closing Reaction)

After the completion of the preliminary reaction, the reactor was cooled to a temperature of 60° C. and then 50 wt. % NaOH 511 g (12.772 mol) was uniformly added dropwise for 2 hours using a funnel while maintaining the degree of vacuum of 120 to 140 Torr and 60° C. During the reaction for 2 hours, water was generated and water was continuously removed using a decanter facility. After completing the dropwise addition of 50 wt. % NaOH, water was continuously removed with further stirring for 1 hour.

In order to remove unreacted epichlorohydrin, the reaction was performed while raising the reaction temperature to 130° C., and then degassing was carried out under 10 Torr or less. Thereafter, the amount of chlorine in the product (Hy-Cl) was measured.

After the temperature of the reactor was raised to 60° C., 46.9 g of water and 50 wt. % of 31.3 g of NaOH were added and stirred for 2 hours to perform an additional ring-closing reaction (for reference, 1.5 mol of NaOH/mol of hydrolysable chlorine).

At this time, if the chlorine content is 0.1% or more, further ring-closing reaction using NaOH was carried out again, and the reaction was terminated at the time of less than 0.1%.

(3) Post-Treatment 767 g of water was added to the obtained product and stirred for 60 minutes to induce phase separation. After standing for 1 hour, the lower aqueous phase portion was removed. The washing process was performed three times so that the pH of the aqueous phase portion to be removed was 5 to 7.

The oil phase of the upper layer was then recovered and degassed under a vacuum of 10 Torr at 120° C. to produce the title compound.

Comparative Example 1: Preparation of (oxiran-2-yl)methyl Pivalate Using Reaction Solvent By a conventionally known method, (oxiran-2-yl) methyl pivalate was prepared. At this time, the preparation of (oxiran-2-yl) methyl pivalate was carried out in the same manner as in Example 1 except that water/isopropyl alcohol was used as a solvent.

(1) Preliminary Reaction

To a 5 L reactor, 660 g (3.831 mol) of neodecanoic acid, 1418 g (15.326 mol) of epichlorohydrin, 1102 g (18.366 mol) of isopropyl alcohol (IPA) and 550 g (30.555 mol) of water were charged. The inside of the reactor was heated to 55° C. while being purged with nitrogen, 50 wt. % NaOH 62 g (1.55 mol) was uniformly added dropwise. Thereafter, the temperature was raised to 85° C. and stirred for 30 minutes.

(2) Main Reaction (Ring-Closing Reaction)

The reactor was cooled to a temperature of 50° C. and then 50 wt. % NaOH 306 g (7.65 mol) was uniformly added dropwise over 40 minutes, followed by stirring for 40 minutes.

After completion of the reaction, phase separation occurred and the lower aqueous phase portion was removed. Then, in order to remove unreacted epichlorohydrin and the solvent (specifically, isopropyl alcohol), degassing was carried out under a vacuum of 10 Torr at 130° C. Thereafter, the amount of chlorine in the product (Hy-Cl) was measured.

After the temperature of the reactor was raised to 60° C., 50 wt. % NaOH 10.6 g was added and stirred for 90 minutes to perform an additional ring-closing reaction (for reference, 1.5 mol of NaOH/mol of hydrolysable chlorine).

At this time, if the chlorine content is 0.1% or more, further ring-closing reaction using NaOH was carried out again, and the reaction was terminated at the time of less than 0.1%.

(3) Post-Treatment 202 g of water was added to the obtained product and stirred for 60 minutes to induce phase separation. After standing for 1 hour, the lower aqueous phase portion was removed. The washing process was performed three times so that the pH of the aqueous phase portion to be removed was 5 to 7.

The oil phase of the upper layer was then recovered and degassed under a vacuum of 10 Torr at 120° C. to produce the title compound.

Comparative Example 2: Preparation of (oxiran-2-yl)methyl 2-ethylhexanoate Using Reaction Solvent By a conventionally known method, (oxiran-2-yl)methyl 2-ethylhexanoate was prepared. At this time, the preparation of (oxiran-2-yl)methyl 2-ethylhexanoate was carried out in the same manner as in Example 1 except that water/isopropyl alcohol was used as a solvent.

(1) Preliminary Reaction

To a 5 L reactor, 660 g (4.576 mol) of 2-ethylhexanoic acid (2-EHA), 1693 g (18.302 mol) of epichlorohydrin, 1316 g (21.896 mol) of isopropyl alcohol (IPA) and 658 g (36.555 mol) of water were charged. The inside of the reactor was heated to 55° C. while being purged with nitrogen, 50 wt. % NaOH 74.3 g (1.858 mol) was uniformly added dropwise for 25 minutes. Thereafter, the temperature was raised to 85° C. and then stirred for 30 minutes.

(2) Main Reaction (Ring-Closing Reaction)

The reactor was cooled to a temperature of 50° C. and then 50 wt. % NaOH 306 g (9.15 mol) was uniformly added dropwise over 40 minutes, followed by stirring for 40 minutes.

After completion of the reaction, phase separation occurred and the lower aqueous phase portion was removed. Then, in order to remove unreacted epichlorohydrin and the solvent (specifically, isopropyl alcohol), degassing was carried out under a vacuum of 10 Torr at 130° C. Thereafter, the amount of chlorine in the product (Hy-Cl) was measured.

After the temperature of the reactor was raised to 60° C., 50 wt. % NaOH 14.6 g was added and stirred for 90 minutes to perform an additional ring-closing reaction (for reference, 1.5 mol of NaOH/mol of hydrolysable chlorine).

At this time, if the chlorine content is 0.1% or more, further ring-closing reaction using NaOH was carried out again, and the reaction was terminated at the time of less than 0.1%.

(3) Post-Treatment 202 g of water was added to the obtained product and stirred for 60 minutes to induce phase separation. After standing for 1 hour, the lower aqueous phase portion was removed. The washing process was performed three times so that the pH of the aqueous phase portion to be removed was 5 to 7.

The oil phase of the upper layer was then recovered and degassed under a vacuum of 10 Torr at 120° C. to produce the title compound.

Experimental Example 1: Analysis of Physical Properties of the Compound

The intermediates and glycidyl ester compounds prepared in the above Examples and Comparative Examples were analyzed by the following methods, and the results are shown in Table 1 below.

(1) Epoxy Equivalent Weight (EEW)

In order to determine the epoxy equivalent weight, appropriate amounts of the samples prepared in the above Examples and Comparative Examples were taken in an Erlenmeyer with stopper flask and completely dissolved by adding 10 ml of 1, 4-dioxane. Then, after accurately adding 25 ml of 0.2 N HCl (dioxane), the flask was closed with a stopper and 1~2 drops of dioxane was added dropwise to the interface with the flask. After sealing, the mixture was reacted at room temperature for 30 minutes.

Subsequently, the flask and stopper were washed with 10 mL of methyl cellosolve and added to the flask. Thereafter, three drops of cresol red indicator were added, and titrated with 0.1 N NaOH (methanol) solution. At this time, titration ends at the point where the color changes from pink to yellow and then becomes purple. At the same time, a blank test was performed. The epoxy equivalent weight was calculated from the obtained results by the following equation (1).

$$\text{Epoxy equivalent weight (g/eq)} = 10{,}000 \times W/(B-A) \times F \quad \text{[Equation 1]}$$

wherein B is consumption (ml) of 0.1 N NaOH (methanol) at the titration of blind test, A is the consumption (ml) of 0.1N NaOH (methanol) at the titration of the sample, F is the factor of 0.1 N NaOH (methanol)

W is the amount (g) of the sample.

(2) Amount of Hydrolysable Chlorine (Hy-Cl)

Samples of the glycidyl ester compounds prepared in the Examples and Comparative Examples were collected in a 200 ml Erlenmeyer flask while accurately weighing up to 0.1 mg. After 25 ml of 1, 4-dioxane was added to the sample and dissolved, 25 ml of 0.1 N KOH (methanol) solution was added, and a glass cooling tube was attached and then the reaction was carried out in a water bath at 70° C. for 30 minutes.

After the temperature in the reactor was cooled to room temperature, the glass cooling tube was washed with 5 to 10 ml of methanol and added to the flask.

Subsequently, the solution in the Erlenmeyer flask was transferred to a 200 ml beaker, and the inside of the Erlenmeyer flask was washed with the aqueous 80% acetone solution two to three times. Thereafter, the washing solution was added to the beaker and then the total volume was made to be 100 ml.

Next, 3 ml of acetic acid was added and titrated with aqueous 0.01 N $AgNO_3$ solution. At this time, the measurement is performed at two points at the same time. If the difference between the measured values is within 0.003%, such an average value is recorded to the third decimal place. At the same time, a blank test was performed.

The amount of hydrolysable chlorine was calculated based on the following equation (2).

$$\text{Amount of hydrolysable chlorine (\%)} = \{[(V-B) \times 0.01 \times 35.5 \times F]/(1{,}000 \times W)\} \times 100 \quad \text{[Equation 2]}$$

wherein V is the consumption (ml) of 0.01 N $AgNO_3$ at the titration of the sample, B is the consumption (ml) of 0.01 N $AgNO_3$ at the titration of the blind test, F is the factor of 0.01 N $AgNO_3$, W is the amount (g) of the sample.

(3) Total Amount of Chlorine (Total-Cl)

In order to measure the total amount of chlorine, the samples of the glycidyl esters prepared in the above Examples and Comparative Examples were collected and accurately weighed in a joint Erlenmeyer flask thoroughly washed with ion exchange water.

Subsequently, the samples were dissolved in 30 ml of 1, 4-dioxane and exactly 5 ml of the solution of 1N KOH (methyl cellosolve) was added.

Next, reflux cooling tube was attached and then the mixture, when refluxing, was heated on a hot plate for 20 minutes, cooled to room temperature, and the cooling tube was washed with 5 ml of methanol and added to the flask.

Next, after washing, the entire amount was transferred to a 200 ml beaker and the used flask was washed with an aqueous 80% acetone solution two to three times and then the total amount was made to be 100 ml. Thereafter, 3 ml of acetic acid was added, and then a potentiometric titration was performed with an aqueous 0.01 N $AgNO_3$ solution. At the same time, a blank test was performed.

The total amount of chlorine was calculated from the results obtained based on the following equation (3).

$$\text{Total amount of chlorine (\%)} = \{[(V-B) \times 0.01 \times 35.5 \times F]/(1{,}000 \times W)\} \times 100 \quad \text{[Equation 3]}$$

wherein V is the consumption (ml) of 0.01 N $AgNO_3$ at the titration of the sample, B is the consumption (ml) of 0.01 N AgNO₃ at the titration of the blind test, F is the factor of 0.01N AgNO₃, W is the amount (g) of the sample.

(4) Yield

The yield was calculated according to the following equation (4).

Yield (%)=$P/R \times 100$         [Equation 4]

wherein P is the content (g) of the finally obtained product, and

R is the total content (g) in which the product is theoretically 100% produced.

The values measured by the methods described above are summarized in Table 1 below.

TABLE 1

|  | Main reaction | | Post-treatment | | | |
| --- | --- | --- | --- | --- | --- | --- |
|  | Epoxy equivalent weight (g/eq) | Amount of hydrolysable chlorine (Hy-Cl, %) | Epoxy equivalent weight (g/eq) | Amount of hydrolysable chlorine (Hy-Cl, ppm) | Total amount of chlorine (T-Cl ppm) | Yield (%) |
| Example 1 | 236.58 | 0.25 | 239.59 | 144.8 | 879.3 | 92% |
| Example 2 | 212.7 | 0.45 | 232.54 | 888 | 1618 | 82% |
| Comparative Example 1 | 239.27 | 0.36 | 239.15 | 942.3 | 1445.3 | 84% |
| Comparative Example 2 | 214.6 | 0.47 | 233.02 | 901 | 1694 | 81% |

In Table 1, the amount of the hydrolysable chlorine means that there are many epichlorohydrin unreacted materials and by-products and the large value means that the content of the impurities in the final product is large. In addition, the total amount of chlorine means the remaining chlorine, which is predicted as a by-product after the completion of the reaction. A large value of the total amount of chlorine means that the content of impurities in the final product is large Referring to Table 1, when comparing the amount of hydrolysable chlorine and the total amount of chlorine of the glycidyl ester compounds of Example 1 and Comparative Example 1 according to the present invention, the value of the compound of Example 1 was very low. It can be seen from these results that the method according to the present invention had very little effect on the production of side-reaction products and unreacted materials. In particular, it can be seen that in the case of the compound of Example 1, it was possible to prepare at a higher yield than the compound of Comparative Example 1.

This tendency was also the same for the comparison of Example 2 and Comparative Example 2.

Experimental Example 2: Analysis of Unit Output

The compounds produced in the Examples and Comparative Examples were analyzed as follows to calculate the unit output, and the results are shown in Table 2 below. The unit output was calculated as the amount of the compound produced in the 5 L reactor and was calculated assuming that the content of the final compounds of Comparative Example 1 was 100%.

TABLE 2

|  | Unit output (g/5 L) | Relative comparison (%) |
| --- | --- | --- |
| Example 1 | 1325 g | 151.4% |
| Example 2 | 1527 g | 166.7% |

TABLE 2-continued

|  | Unit output (g/5 L) | Relative comparison (%) |
| --- | --- | --- |
| Comparative Example 1 | 875 g | 100% |
| Comparative Example 2 | 916 g | 100% |

Referring to Table 2, it can be seen that when the method of Example 1 is performed to prepare the same compound, the unit output of 51.4% relative to the method of Comparative Example 1 was increased.

It can be seen that this tendency was also the same for the comparison of Example 2 and Comparative Example 2, and the unit output of 66.7% relative to the method of Comparative Example 2 was increased in Example 2.

These results are calculated in a 5 L reactor. When applied to the mass production process of the plant unit, the above 51.4% value means a very large difference.

INDUSTRIAL APPLICABILITY

The method of preparing the glycidyl ester compound according to the present invention has greatly improved unit output and thus it can be suitably applied to a mass production process.

The invention claimed is:

1. A method for preparing a glycidyl ester compound of Formula 1, which comprises reacting a carboxylic acid compound of Formula 2 and an epihalohydrin of Formula 3 under reduced pressure without use of a reaction solvent, as set forth in the following Reaction Scheme 1:

Reaction Scheme 1

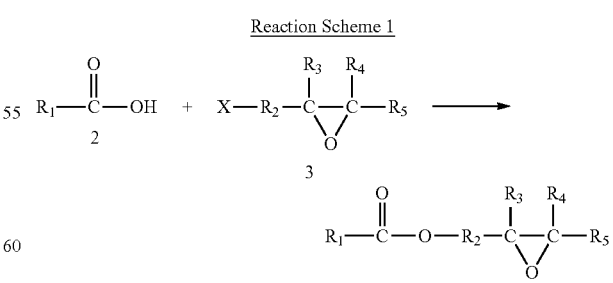

wherein $R_1$ is a C1 to C20 alkyl group, a C2 to C20 alkenyl group, a C2 to C20 alkynyl group, a C1 to C20 alkoxy group, a C3 to C20 cycloalkyl group, a C5 to C40 heteroaryl group, a C6 to C40 aryl group, a C6 to C20 alkoxyaryl group, or a C6 to C20 arylalkyl group, $R_2$ is a C1 to C20 alkylene group, C1 to C20 alkenylene group, C3 to C20 cycloalkylene group, or C6 to C40 arylene group, $R_3$ to $R_5$ are the same or different from each other and are hydrogen or a C1 to C20 alkyl group, and X is a halogen;

wherein the reacting comprises a preliminary reaction step S1) of reacting the carboxylic acid compound of Formula 2 and the epihalohydrin of Formula 3 in the presence of a base catalyst without the use of a reaction solvent to perform a ring-opening reaction to produce a ring-opening reaction product, and wherein the preliminary reaction step S1) is carried out at a temperature of from 80 to 100° C.

2. The method for preparing the glycidyl ester compound according to claim 1, wherein $R_1$ is

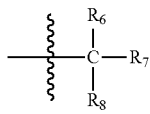

wherein $R_6$ to $R_8$ are the same or different from each other and are hydrogen or a C1 to C20 alkyl group.

3. The method for preparing the glycidyl ester compound according to claim 1, wherein the reacting further comprises, after the preliminary reaction step S1)

a main reaction step S2) of adding the base catalyst to the ring-opening reaction product and carrying out a ring-closing reaction under reduced pressure to give a ring-closing reaction product; and a step S3) of post-treating the ring-closing reaction product.

4. The method for preparing the glycidyl ester compound according to claim 3, wherein the carboxylic acid compound of Formula 2 and the epihalohydrin of Formula 3 are reacted in a molar ratio of from 1:1.2 to 1:5.0.

5. The method for preparing the glycidyl ester compound according to claim 3, wherein the base catalyst of step S1) and step S2) comprises at least one selected from the group consisting of LiOH, NaOH, KOH, Ca(OH)$_2$, Mg(OH)$_2$, K$_2$CO$_3$, Na$_2$CO$_3$, KHCO$_3$, and NaHCO$_3$.

6. The method for preparing the glycidyl ester compound according to claim 3, wherein the reduced pressure is from 50 to 200 Torr.

7. The method for preparing the glycidyl ester compound according to claim 3, wherein the main reaction step S2) is carried out at a temperature of from 35 to 90° C.

8. The method for preparing the glycidyl ester compound according to claim 3, further comprising performing a degassing process between the main reaction step S2) and the post-treatment step S3) at a temperature of from 110 to 150° C. under a pressure of 10 Torr or less.

9. The method for preparing the glycidyl ester compound according to claim 3, further comprising performing an additional ring-closing reaction by adding the base catalyst to the ring-closing reaction product, before the post-treatment step S3).

10. The method for preparing the glycidyl ester compound according to claim 3, wherein the post-treatment step S3) is carried out by at least one of desalting, neutralization, water washing, filtration, purification, concentration, crystallization, and drying.

* * * * *